(12) United States Patent
Speier

(10) Patent No.: US 6,815,950 B2
(45) Date of Patent: Nov. 9, 2004

(54) J-SPECTROSCOPY IN THE WELLBORE

(75) Inventor: Peter Speier, Erlangen (DE)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/064,529

(22) Filed: Jul. 24, 2002

(65) Prior Publication Data

US 2004/0017193 A1 Jan. 29, 2004

(51) Int. Cl.$^7$ ................................................ G01V 3/00
(52) U.S. Cl. ....................................... 324/303; 324/300
(58) Field of Search ................................ 324/303, 300, 324/307, 309, 314, 318, 377

(56) References Cited

U.S. PATENT DOCUMENTS

| | | | | |
|---|---|---|---|---|
| 5,043,664 A | * | 8/1991 | Kunz | 324/307 |
| 5,677,628 A | * | 10/1997 | Watanabe et al. | 324/309 |
| 5,955,883 A | * | 9/1999 | Hennig | 324/307 |
| 6,111,409 A | * | 8/2000 | Edwards et al. | 324/303 |
| 6,147,490 A | | 11/2000 | Watanabe | |
| 6,184,683 B1 | * | 2/2001 | Emsley et al. | 324/309 |
| 6,294,914 B1 | * | 9/2001 | Fiat | 324/312 |
| 6,346,813 B1 | * | 2/2002 | Kleinberg | 324/303 |

* cited by examiner

Primary Examiner—Brij B Shrivastav
(74) Attorney, Agent, or Firm—Kevin P. McEnaney; Brigitte L. Jeffery; John J. Ryberg (57) ABSTRACT

An NMR instrument for determining formation fluid properties includes a housing adapted to move in a wellbore; a magnet disposed in the housing adapted to induce a static magnetic field; an antenna assembly disposed in the housing adapted to resonate at a first frequency and a second frequency, the first frequency corresponding to a resonance frequency of a first nucleus, the second frequency corresponding to a resonance frequency of a second nucleus, wherein the first nucleus is different from the second nucleus; means for inducing an RF magnetic field; and means for detecting NMR signals at the first frequency. A method of NMR measurement includes inducing a static magnetic field having a selected magnetic field strength in an earth formation sample; acquiring NMR measurements having J coupling information; and deriving the J coupling information from the NMR measurements.

42 Claims, 7 Drawing Sheets

J-SPECTROSCOPY IN THE WELLBORE

BACKGROUND OF THE INVENTION

Oil and gas exploration and production are very expensive operations. Any knowledge about the formations that can help reduce the unnecessary waste of resources in well drilling will be invaluable. Therefore, the oil and gas industry have developed various tools capable of determining and predicting earth formation properties. Among different types of tools, nuclear magnetic resonance (NMR) instruments have proven to be invaluable. NMR instruments can be used to determine formation properties, such as the fractional volume of pore space and the fractional volume of mobile fluid filling the pore space.

Nuclear magnetic resonance is a phenomenon occurring in a selected group of nuclei having magnetic nuclear moments, i.e., non-zero spin quantum numbers. Common nuclei with magnetic moments ("nuclear spins") include $^1$H (proton), $^{13}$C (carbon-13), $^{19}$F (fluorine-19) and $^{31}$P (phosporus-31). Hereafter, "nuclear spins" will be used to refer to magnetic moments of nuclei. When these nuclei are placed in a magnetic field ($B_o$, "Zeeman field"), they each precess around the axis of the $B_o$ field with a specific frequency, the Larmor frequency ($\omega_o$), which is a characteristic property of each nuclear species (gyromagnetic ratio, $\gamma$) and depends on the magnetic field strength ($B_o$) effective at the location of the nucleus, i.e., $\omega_o = \gamma B_o$.

A typical NMR tool comprises a device that is moveable in a well bore. The device comprises a permanent magnet, which is used to induce a static magnetic field that aligns the nuclei of interest along the axis of the magnetic field (which is conventionally referred to as the Z-axis), and an antenna, which is used to provide radio frequency (RF) pulses and to act as a receiver for the resulting resonance signals. The RF pulses transmitted through the antenna produce a magnetic field ($B_1$ magnetic field) which realigns the nuclei in a different orientation. Conventionally, the RF magnetic field is applied in the X or –X axis direction. This results in the net magnetization of the nuclei (nuclear spin) to mutate towards the –Y or Y axis, respectively. The X and Y axes refer to the axes in the rotating frame that is customary in the art. In a conventional spectrometer, the receiver is designed to measure the Y-axis and/or X-axis component of the magnetization as the latter precesses around the Z axis.

In a typical application, the RF pulse strength is controlled such that the nuclear spins are realigned onto a plane which is perpendicular to the direction of the magnetic field generated by the permanent magnet. Such RF pulse is called a 90-degree pulse because it nutates nuclear spins by 90 degrees (from the Z-axis to the Y-axis). Similarly, a pulse that nutates the nuclear spins from the Z-axis to the Z axis direction is referred to as a 180-degree pulse. Once in this perpendicular plane, the interactions between the static magnetic field and the nuclei cause these nuclei to precess around the static magnetic field axis with a characteristic frequency called Larmor frequency. The precessing of these nuclei produces signals that are detected by the antenna. In the absence of further perturbation, these nuclei will gradually return to their steady states, in which their net spin moments are aligned with the static magnetic field. The process of this return to the steady state is referred to as the spin-lattice (longitudinal) relaxation and is defined by a life time called T1. A separate process, spin-spin (transverse) relaxation, is also available by which the nuclear spins lose their detectable magnitudes. The spin-spin relaxation is defined by a lifetime T2, which is typically less than or equal to T1. T2 relaxation is typically investigated with pulse sequences that permit acquisition of NMR data that are more suitable for T2 relaxation analysis, e.g., a Carr-Purcell-Meiboom-Gill (CPMG) sequence. The signal magnitudes measured by a CPMG sequence decay exponentially by the spin-spin relaxation mechanism. The T1 and T2 values reflect the chemical and physical properties of the observed nuclei. Therefore, they can provide information as to the properties and the environment of the nuclei.

Most NMR tools used in earth formation analysis measure the spin-lattice relaxation times (T1) or spin-spin relaxation times (T2) to derive the properties of the earth formations. T2 relaxation is often measured from a train of spin-echoes that are generated with a series of pulses such as the Carr-Purcell-Meiboom-Gill (CPMG) pulse sequence or some variant of this. The CPMG pulse sequence is well known in the art. See Meiboom, S., Gill, D., 1958, *"Modified Spin Echo Method for Measuring Nuclear Relaxation Times,"* Review of Scientific Instruments, 29, 688–91.

A CPMG sequence typically comprises a 90-degree (excitation) pulse followed by a series of 180-degree pulses (refocusing pulses or inversion pulses) with a fixed delay time between them. The delay times between the 180-degree pulses are roughly twice as long as that between the 90-degree and the first 180-degree pulses. The initial 90-degree pulse aligns the nuclear spins in the plane perpendicular to the direction of the magnetic field induced by the permanent magnet. The successive 180-degree pulses keep these nuclear spins roughly in this plane for the duration of the measurement The nuclear spins in the transverse plane decay mainly via the spin-spin relaxation (T2) pathway. Thus, one can derive the T2 relaxation time by analyzing the exponential decay of the spin-echo magnitudes.

NMR logging commonly detects $^1$H (proton) signals because proton is among the most abundant and easily detectable nuclei. These measurements do not include information on the couplings (scalar couplings or J-couplings) between the observed protons and other hetero nuclei because a typical CPMG sequence does not permit acquisition of such hetero coupling information. Scalar couplings or J couplings arise from through bond interactions, in which two nuclei connected by covalent bonds influence each other. Assuming a nucleus A under investigation has a neighbor B located one to three covalent bonds away (e.g., the $CH_3$ and CH protons in acetaldehyde, $CH_3$—CH=O), nucleus A would have its neighbor B in the low-spin state half of the times and in the high-spin state the other half of the times. As a result, the NMR signal of nucleus A would appear as a doublet, separated by a coupling constant J Hz. The magnitude of the J coupling constant depends on the types of nuclei involved and the separation (how many covalent bonds) between the nuclei. If the coupling is between two different types of nuclei (e.g., $^1$H and $^{13}$C), it is referred to as heteronuclear coupling. If it is between the same type of nuclei (e.g., $^1$H and $^1$H), the coupling is homonuclear coupling. Most J couplings are detectable if the coupled nuclei are separated by three or fewer covalent bonds. The closer the coupled nuclei are to each other, the stronger the J couplings are.

The scalar (J) couplings, because they depend on the types of nuclei involved and the separation between the coupled nuclei (and some times the geometry of the molecules), may provide information regarding the structures of the molecules under investigation. For example, the hetero J couplings between C and H are about 125–130 Hz for aliphatic compounds and about 150 Hz for aromatic compounds. This molecular information may be invaluable in characterizing formation fluids. Therefore, it is desirable to have apparatus and methods for formation fluid analysis that can provide scalar coupling information.

SUMMARY OF THE INVENTION

One aspect of the invention relates to NMR instruments for well logging or formation fluid sampling and analysis. These NMR instruments are capable of measuring NMR data that include heteronuclear or homonuclear coupling modulations. A nuclear magnetic resonance instrument according to embodiments of the invention includes a housing adapted to move in a wellbore; a magnet disposed in the housing adapted to induce a static magnetic field having a selected magnetic field strength in a zone of interest; an antenna assembly disposed in the housing, the antenna assembly adapted to resonate at a first frequency and a second frequency, the first frequency corresponding to a resonance frequency of a first nucleus at the selected magnetic field strength, the second frequency corresponding to a resonance frequency of a second nucleus at the selected magnetic field strength, wherein the first nucleus is different from the second nucleus; means for inducing a radio frequency magnetic field according to a selected pulse sequence in the zone of interest, the means for inducing the radio frequency magnetic field being operatively coupled to the antenna assembly; and means for detecting nuclear magnetic resonance signals at the first frequency, the means for detecting being operatively coupled to the antenna assembly.

Another aspect of the invention relates to methods for determining a formation property with a nuclear magnetic resonance instrument in a wellbore using J-spectroscopy. A method according to the invention includes inducing a static magnetic field having a selected magnetic field strength in an earth formation sample; acquiring nuclear magnetic resonance measurements having J coupling information using the nuclear magnetic resonance instrument; and deriving the J coupling information from the nuclear magnetic resonance measurements. The acquiring NMR measurements may be performed with a pulse sequence comprising a CPMG pulse sequence.

Other aspects and advantages of the invention will be apparent from the following description and the appended claims.

DETAILED DESCRIPTION

Formation analysis may use various types of tools. Some tools (i.e., logging tools) survey the earth formations without removing samples from their natural environments, while others (e.g., formation fluid sampling tools) extract samples from the formations to perform analysis out side of their natural environments. NMR instruments have been used in both types of tools. In well logging operations, NMR instruments may be used in a wireline tool or a logging-while-drilling (LWR or MWD, measurement-while-drilling) tool. For example, U.S. Pat. No 4,717,878 issued to Taicher et al. and U.S. Pat. No. 5,055,787 issued to Kleinberg et al disclose a wireline NMR tools, and U.S. Pat. No. 5,280,243 issued to Melvin Miller and U.S. Pat. No. 5,757,186 issued to Taicher et al. disclose MWD NMR tools. For formation dynamics testing, NMR instruments have been incorporated in formation fluid sampling tools to analyze properties of hydrocarbons. For example, U.S. Pat. No. 6,111,409 issued to Edwards et al. and U.S. Pat. No. 6,346,813 B1 issued to Kleinberg disclose formation fluid testing tools that include NMR modules for analysis of connate fluids removed from the formations.

Figures 1, 3:
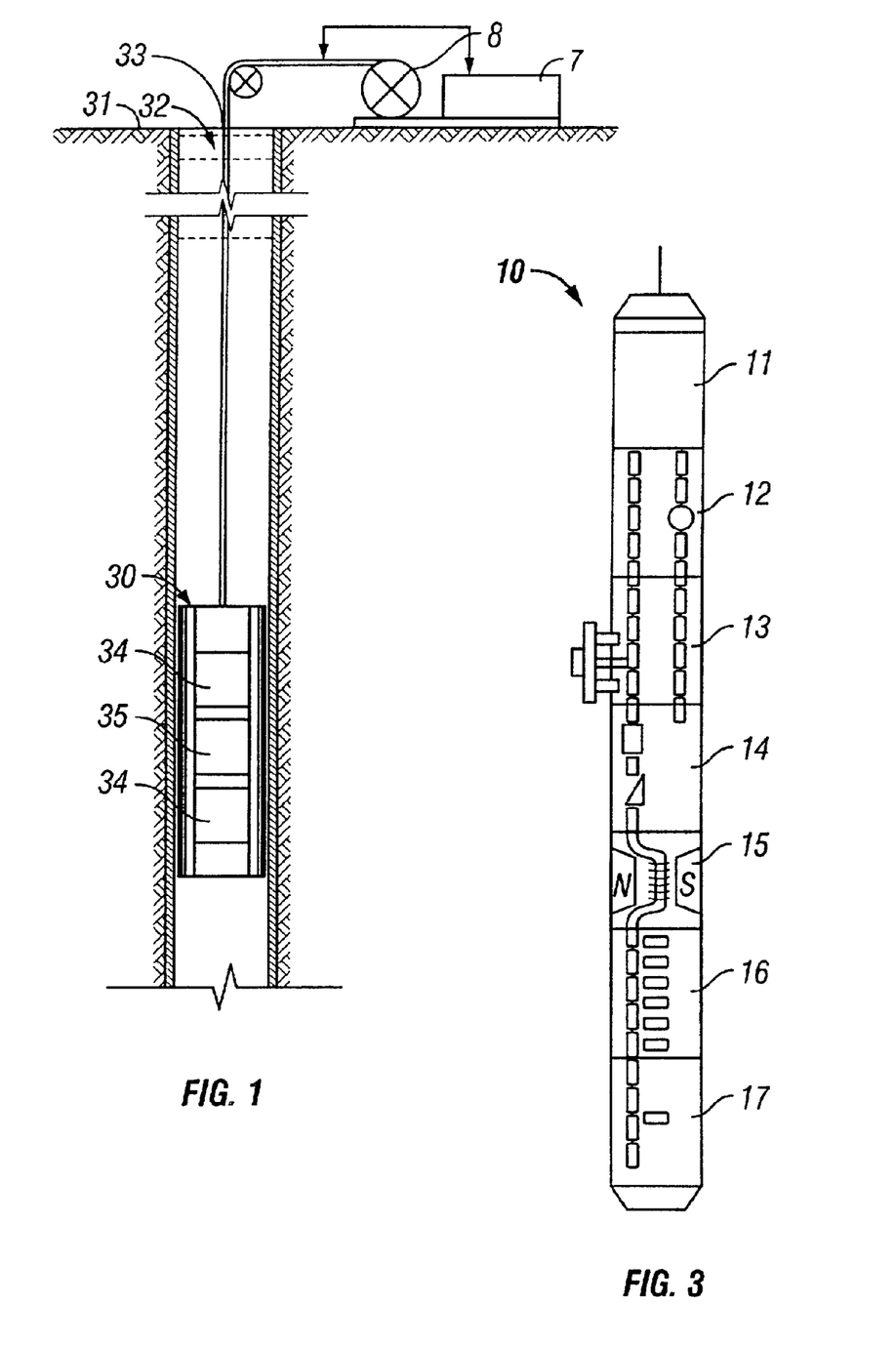
FIG. 1 is a diagram of prior art an NMR logging tool.
FIG. 3 illustrates a schematic diagram of a fluid sampling tool utilized in extracting formation fluid in accordance with the invention.

FIG. 1 illustrates a schematic of an NMR well logging tool 30 placed in a wellbore 32 that penetrates a formation 31. The NMR logging tool 30 is suspended in well bore 32 on an armored cable 33, the length of which substantially determines the relative depth of the tool 30. The cable length is controlled by suitable means at the surface such as a drum and winch 8. Surface equipment 7 may comprise a processor which communicates with the downhole equipment. Although a wireline tool is shown in FIG. 1, variations of NMR logging tools may include MWD tools. The tool 30 may include one or more permanent magnets, represented as block 34, and one or more antennae, represented as block 35, that can induce RF magnetic field and function as receivers.

Figure 2:
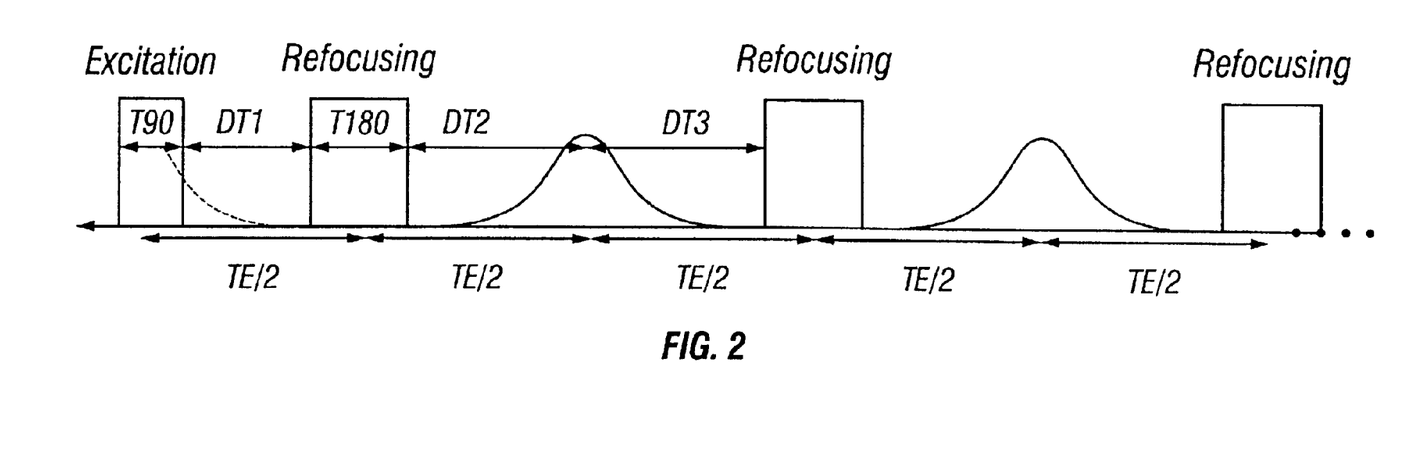
FIG. 2 shows a diagram of a typical CPMG pulse sequence.

FIG. 2 shows a typical CPMG pulse sequence, which comprises a 90-degree excitation pulse (T90) followed by a delay (TE/2) and a train of 180-degree pulses (T180) separated by delay times (TE). The T180 pulses are also referred to as refocusing pulses. Before application of the CPMG sequence, nuclear spins under investigation align with the direction of the static magnetic field, which is conventionally denoted as the Z-axis direction. When the T90 excitation pulse is applied to the spin system, the nuclear spins are nutated onto the transverse plane (the XY plane). Afterwards, the nuclear spins begin to re-equilibrate back to the steady state. There are two main processes by which the nuclear spins can re-equilibrate back to the steady state: spin-lattice (T1) relaxation and spin-spin (T2) relaxation. These relaxation processes are first-order processes, which give rise to exponentially decreasing magnitudes of the detectible signals.

Each of the two relaxation processes may be investigated using special pulse sequences. For T1 measurements, commonly used pulse sequences include inversion recovery and saturation recovery. With inversion recovery, the spin magnetizations are inverted by a 180-degree pulse and the signals are acquired after various delay times that permit monitoring of the progression of return of the magnetization back to the steady state. With saturation recovery, a strong RF magnetic field is applied to cause complete equalization of the spin state populations, and the signals are monitored as a function of time after the saturation pulse is turned off and the spins are allowed to return to the steady state. For T2 measurements, commonly used pulse sequences include those that substantially suppress dephasing due to inhomogeneities. These pulse sequences may include Han spin-echo pulse sequence, Carr-Purcell pulse sequence (i.e., without Meiboom-Gill modification), CPMG pulse sequence, and phase-cycled CPMG pulse sequence.

In a CPMG pulse sequence, the train of 180-degree pulses (T180 in FIG. 2) functions to suppress dephasing due to inhomogeneities, while the TE delay times between the T180 pulses permit monitoring of the spin echoes. The magnitudes of the series of spin echoes decrease exponentially by the spin-spin relaxation process. Thus, T2 information may be obtained from the exponential decays of the spin echo magnitudes as a function of time.

While the prior art pulse sequences used in well logging or formation fluid testing provide measurements of T1 and T2 relaxation times, they do not provide information on scalar couplings (homo or hetero couplings) for the following reasons: (1) these measurements are homonuclear (single channel) experiments; they cannot detect any heteronuclear coupling information; and (2) $^1H$—$^1H$ couplings are small (typically 0–18 Hz) and are more difficult to detect. Logging tools typically have magnetic field gradients. To suppress additional signal decays due to diffusion, spin echo data are obtained with rapid pulses, e.g., the inter-echo delay TE is typically on the order of milliseconds or less. If TE<$1/\Delta\omega$, where $\Delta\omega$ is the Larmor frequency difference between the coupled nuclei, then homonuclear J modulation can be suppressed. Thus, J modulation information cannot be derived from data obtained in standard logging. Furthermore, most signals measured with a logging or formation tester tool decay with short T2. These signals may decay before $^1H$—$^1HJ$ modulation has time to develop. This problem is more severe with well logging because nuclear species in the formations have shorter T2 due to surface relaxivity.

An approach to circumvent the potential problem of magnetic field inhomogeneity in the earth formations is to withdraw the samples from the formations and analyze them outside of their original environments. Many tools known in the art are capable of withdrawing samples from the formations for analysis. These tools will be generally referred to as "formation fluid sampling tools." For example, U.S. Pat. Nos. 4,860,581 and 4,936,139 both issued to Zimmerman et al. disclose down hole tools that extract samples for determining formation properties such as permeability and pressure profile. These patents were assigned to the same assignee as the present invention and are hereby incorporated by reference. These tools may have modules that can perform different analysis. Examples of such tools include Modular Formation Dynamics Testers sold under the trade name of MDT™ by Schlumberger Technology Corporation (Houston, Tex.). The modules on MDT™ may include an NMR instrument. For example, U.S. Pat. No. 6,346,813 B1 issued to Kleinberg discloses one such MDT™ tool. In addition, U.S. Pat. No. 6,111,409 issued to Edwards et al. discloses an NMR tool that measures $^{13}C$—NMR spectra of samples removed from the formations.

Modern fluid sampling tools are composed of several parts which enable extraction of fluids from permeable earth formations. FIG. 3 shows one example of a fluid sampling tool 10 having several modules with different functions. The electric power module 11 and the hydraulic power module 12 power the tool. The probe module 13 is deployed so as to make a hydraulic seal with the formation. The seal makes it possible to withdraw connate fluids free from contaminations from the drilling mud. Tool 10 also has a pumpout module 17, which lowers the pressure in the flow line in a controlled manner so as to extract fluids from the formations while maintaining the pressure near the original formation pressure. Samples are optionally monitored by an optical fluid analyzer (OFA) 14 and/or other monitoring devices (not shown) that can monitor the properties (pressure, acidity, resistivity, etc.) of the withdrawn fluids. These monitoring devices are used to indicate when the fluids being withdrawn are free from contaminations by the drilling mud or mud filtrate and when the fluids can be retained for transportation to surface laboratories in the multisample module 16.

The modular design of such tools permits other analysis and monitoring devices to be incorporated in these tools. For example, NMR module 15 may be included in fluid sampling tool 10. The NMR module, like a regular NMR well logging instrument, would include at least one permanent magnet (shown as N and S poles) for inducing static magnetic fields in the sample chamber and at least one antenna (not shown) for generating radio frequency magnetic field pulses and for receiving the NMR signal amplitudes. U.S. Pat. No. 6,346,813 B1 issued to Kleinberg discloses one such tool with an NMR module for conventional NMR measurements. This patent is assigned to the same assignee as the present invention and is hereby incorporated by reference.

For NMR analysis, formation fluid sampling tools has the advantage of being able to achieve better magnetic field homogeneity as compared with NMR logging tools. Better magnetic field homogeneity makes certain measurements possible, e.g., resolving chemical shift differences. On the other hand, NMR logging tools have the advantage of detecting samples in their native environments and permit estimation of formation properties such as total formation porosities, bound fluid volumes, and free fluid volumes. Embodiments of the invention may use with type of these tools.

While the prior art NMR tools, whether logging tools or formation fluid sampling tools, typically measure NMR relaxation times or chemical shifts, methods according to the invention are capable of measuring NMR scalar coupling (also called J coupling) data. Because J coupling is independent of static field homogeneity, these methods may also be used in the presence of imperfect magnetic fields, $B_o$ and $B_1$. Methods according to the invention may be generally referred to as J-spectroscopy and the NMR data thus obtained as J-modulated NMR data.

J-spectroscopy refers to spectroscopy that relies on coupling modulation of the NMR signals. Coupling modulation of NMR signals becomes observable when a delay time long enough for the J modulation to evolve is inserted between a detection (or excitation) pulse (which is typically a 90-degree pulse) and the start of data acquisition. Thus, a pulse sequence for J-spectroscopy in the simplest form may comprise a 90-degree pulse followed by a delay period (evolution period, TE) before data acquisition. In practice, a 180-degree pulse is typically applied to both the observed and the coupled nuclei at halfway through the evolution period (TE) to refocus the chemical shifts, while preserving the J modulation. The most commonly known J-spectroscopy relates to two-dimensional NMR experiments involving homo-nuclear couplings (e.g., $^1H$—$^1H$ coupling). However, the same principle applies to hetero-nuclear situations (e.g., $^1H$—$^{13}C$ coupling). In a typical 2D J-coupling experiment, the measurement is repeated for different delay values (evolution times) until a sufficient range of delay values is covered so that the suite of data may be analyzed for J modulation. This is different form observing the modulation from echo to echo after one excitation as in a CPMG sequence.

Figure 4:
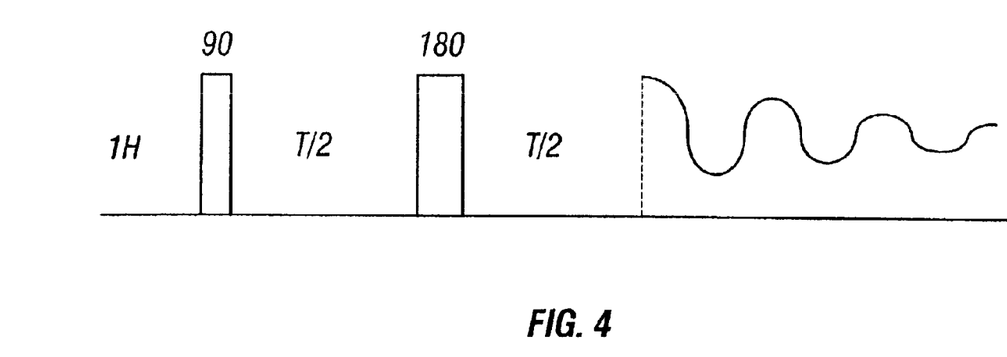
FIG. 4 shows a diagram of a simple pulse sequence for homonuclear J-spectroscopy.
Figure 5:
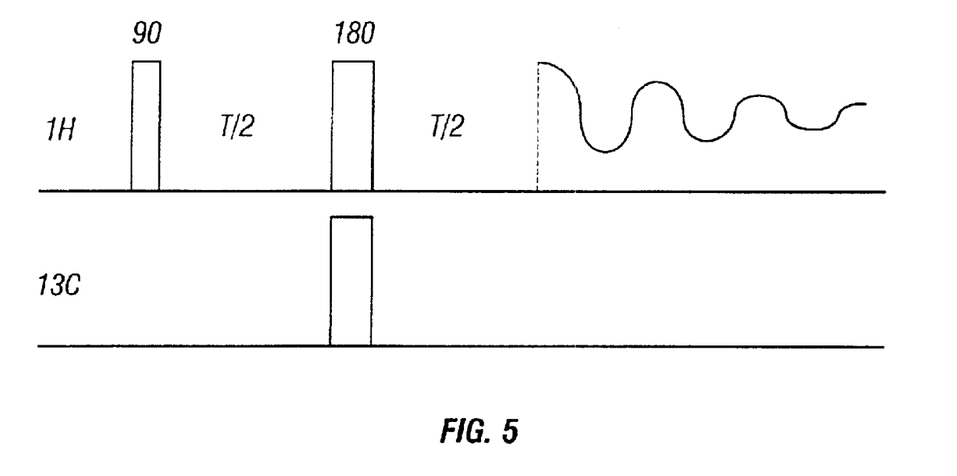
FIG. 5 shows a diagram of a simple pulse sequence for heteronuclear J-spectroscopy.

FIG. 4 shows a pulse sequence for a simple homonuclear J-spectroscopy experiment. A corresponding pulse sequence for heteronuclear J-spectroscopy is shown in FIG. 5. Note that in the heteronuclear case (e.g., $^1$H—$^{13}$C couplings), a separate 180-degree pulse at the coupled nuclear frequency is required when the 180-degree refocusing/inversion pulse is applied to the observed nuclei. Without the inversion of the coupled spins by the 180-degree pulse, the J-modulation will be lost by the 180-degree refocusing/inversion pulse at the observed spins. The 180-degree pulses are best applied simultaneously. However, it is also possible to obtain J-modulated measurements if the 180-degree pulses are applied close in time, i.e., substantially simultaneously or the temporal separation between the 180-degree $^1$H pulse and the corresponding 180-degree $^{13}$C pulse is less than one half the inter-echo delay time. The simultaneous inversion (by 180-degree pulses) of both the observed and the coupled nuclei is achieved by a single 180-degree pulse at the frequency of the observed nuclei in the homonuclear case.

The principles of J-spectroscopy can be explained using product operator formalism, whether in a homonuclear or heteronuclear situation. The following discussion will use homonuclear J-spectroscopy as an example. One skilled in the art would appreciate that the same principles apply to heteronuclear spectroscopy. Assuming the spin system is at thermal equilibrium, the initial longitudinal magnetization (nuclear spins) just before the 90-degree pulse for a weakly coupled two-spin system may be described by: $I_Z+S_Z$, where $I_Z$ represents the Z component of the nuclear spins under investigation (I) and $S_Z$ represents the Z component of the nuclear spin (S) that is coupled to I. This general formulation is applicable to both homo- and hetero-nuclear coupling systems. A 90-degree pulse along the X axis direction then creates transverse magnetization in the -Y axis direction for both I and S (because I and S are the same nuclear species in a homonuclear experiment and are affected by the 90-degree pulse in the same manner). This is described by the product operator formalism as follows:

$$I_z + S_z \xrightarrow{\pi/2(I_X)+\pi/2(S_X)} -I_Y - S_Y$$

Note that in a heteronuclear experiment, only the observe nuclei ($I_z$) are excited and converted into transverse magnetizations ($-I_y$), while the coupled nuclei ($S_z$) remain as longitudinal magnetizations. This still permits development of J modulation in the observe nuclei ($-I_y$). In this case, the coherence is limited by the longer T1 relaxation time, not the T2 relaxation time, of the coupled nuclei ($S_z$).

During the subsequent evolution period, it is necessary only to consider the effect of the spin-coupling Hamiltonian, because chemical shift terms are refocused by the 180-degree pulse. At the end of the evolution period (t), the spin system is as follows:

$$-I_Y - S_Y \xrightarrow{2\pi J t I_Z S_Z} -I_Y \cos\pi Jt + 2I_X S_Z \sin\pi Jt - S_Y \cos\pi Jt + 2S_X I_Z \sin\pi Jt$$

It is apparent from the above equation that the observable terms of both the I and S species, $I_Y$ and $S_Y$, are modulated by a cosinusoidal function in J during the evolution period (t). This is commonly known as J-modulation in conventional spin-echo spectra. The mixed terms ($I_X S_Z$ and $S_X I_Z$) on the right-hand side of the equation do not formally constitute the observables, but they will evolve into the observables in $I_Y$ and $S_Y$ during the time period of data acquisition, with a sinusoidal dependence on J during the evolution period. See S. W. Homans, *A dictionary of Concepts in NMR*, pp. 176-78, revised edition, Clarendon Press, Oxford, UK (1993).

As shown in the above equation, coupling modulations of the observed signals are cosinusoidal with periodicities that depend on the products of the coupling constants (J) and the evolution period (t). For the k-th echo in a CPMG measurement, the evolution period (t) equals k*TE, where TE is the inter-echo delay. Knowing the evolution period (t), it is possible to extract the coupling constants (J) from the periodicities of the modulations. The coupling constants in turn can be used to derive the properties of the molecules under observation. For example, $^1$H—$^{13}$C couplings are typically in the following ranges: methyl groups (CH$_3$) $J_{CH}\approx$125 Hz, aliphatic hydrocarbons $J_{CH}\approx$125–145 Hz, and unsaturated hydrocarbons (double bonds and triple bonds) and aromatic groups $J_{CH}\approx$150–200 Hz. These distinctive coupling constants contain information about, for example, aromatic group content, double bond content, methyl group content or content of spin nuclei other than C and H, such as N. This J coupling finger print may be used, possibly in conjunction with other information, such as NMR relaxation times, optical and mechanical properties, to evaluate crude oils. Even if various J coupling components cannot be resolved, for example, because J-modulation cannot be measured with a sufficient number of echoes due to short relaxation times, the volume fraction of oils can be determined from the total magnitude of the C—H J-coupling modulation spectrum as compared with the overall magnitudes of the NMR measurements. For example, at natural abundance, there should be 1.1% C—H J-coupling modulated part in the overall NMR signal magnitudes, if the earth formation fluid is comprised of 100% oils (hydrocarbons). An NMR measurement having only 0.55% C—H J coupling modulated part would indicate that the sample comprises 50% hydrocarbons and 50% aqueous phase (e.g., brine).

The above illustration shows that in a J-spectroscopy experiment, the observed signals are modulated by the scalar J couplings according to a sinusoidal or cosinusoidal function. This modulation may be directly detected in a conventional chemical shift spectrum, such as two-dimensional (2D) J-spectroscopy. However, obtaining the J-modulation information from one-dimensional chemical shift spectra is possible only if the coupled signals can be resolved. Resolution of coupled signals (especially $^1$H homonuclear coupled signals) requires a highly homogeneous static magnetic field ($B_o$), which is difficult to achieve in downhole environments. For this reason, the J-modulation may be more conveniently retrieved from the CPMG-type spin echo measurements. The following discussion will use a typical CPMG and a modified CPMG experiments to illustrate this approach.

Figure 6:
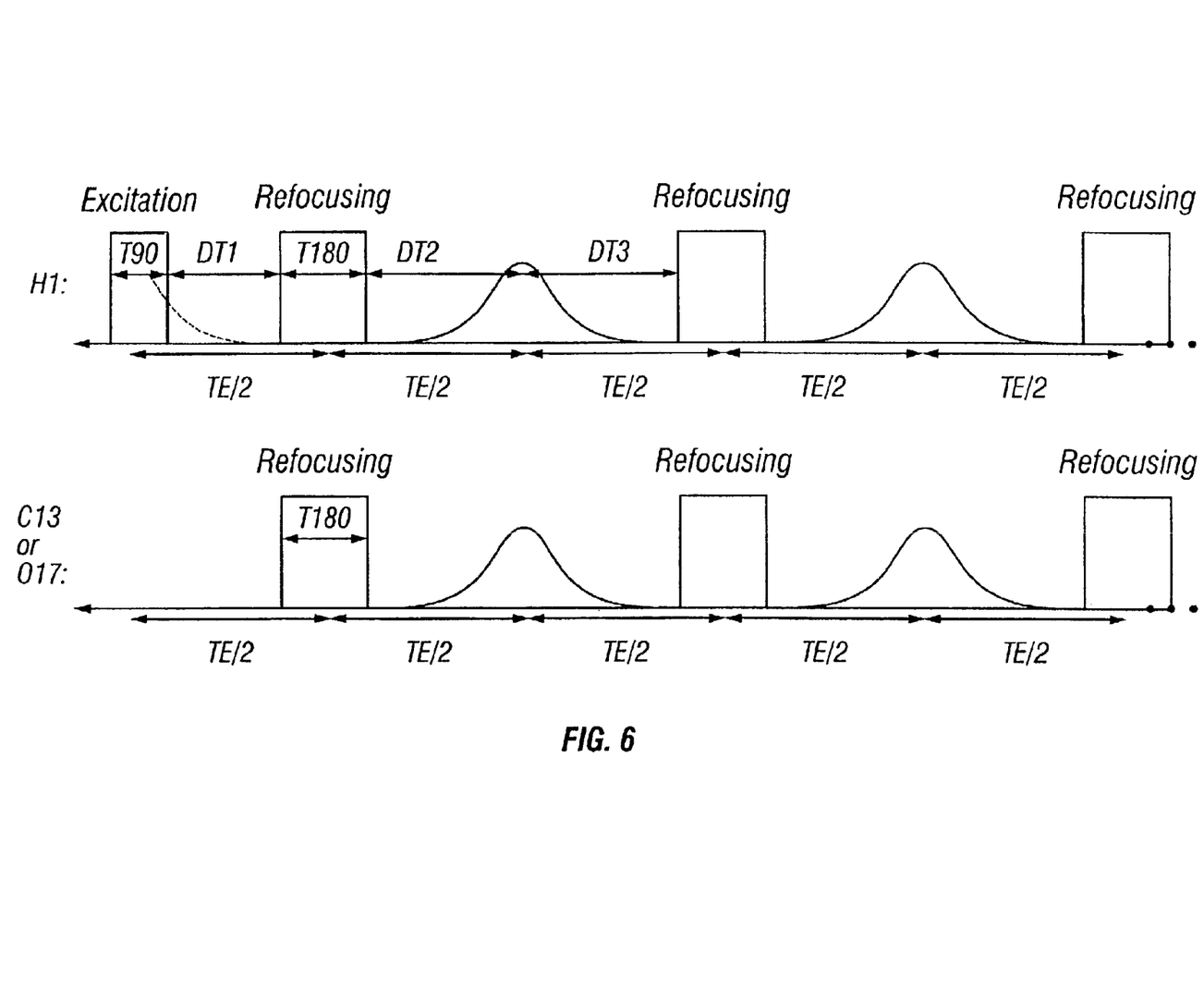
FIG. 6 shows a diagram of a pulse sequence for acquiring spin echo measurements that include J modulations.

FIG. 6 illustrate a pulse sequence that combines J-spectroscopy with CPMG measurements. The pulse sequence comprises a CPMG pulse sequence at the observed nucleus frequency and an 180-degree pulse train at the coupled nucleus frequency. The 180-degree pulse train at the coupled nucleus frequency substantially coincides with the corresponding 180-degree pulse train in the CPMG pulse sequence. In this example, the observed nucleus is $^1$H and the coupled nucleus is $^{13}$C. However, methods according to the present invention are applicable to other nuclear coupling systems. In FIG. 6, the first echo is acquired with a simple spin-echo sequence as that shown in FIG. 5 for a heteronuclear J-spectroscopy. The simple spin-echo sequence is followed by a series of 180-degree pulses at both the observed and the coupled nuclei. The delay time (inter-echo delay time, TE) times the total number of echoes (NE) collected (total data acquisition time in a CPMG pulse sequence) should be such that sufficient J modulation could occur. This requirement is met if TE×NE is appreciable (or greater than) as compared to 1/J. This requirement is to ensure that enough data are collected to substantially define at least one period of a sinusoidal wave that arises from the J modulation. The upper limit of TE×NE may be limited by (1) the detectable magnitudes of the signals, which are determined by their relaxation rates; and (2) decay due to diffusion in magnetic field gradients (or inhomogeneities) for a given TE. The detectable magnitudes of the signals limit the number of spin echoes that are detectable in a CPMG pulse sequence.

The above description concerns the observation of J couplings. Some embodiments of the invention relate to distinguishing different J couplings. In other words, these embodiments concern differences in the coupling constants, $|J_1-J_2|$, where $J_1$ and $J_2$ are different coupling constants. For example, one may be interested in distinguishing the aliphatic contents (J≈125–140 Hz) from aromatic contents (J≈150–200 Hz) in crude oils. In order to distinguish $J_1$ and $J_2$, NE×TE must be on the order of $1/|J_1-J_2|$.

For heteronuclear couplings between $^1H$ and $^{13}C$, the scalar couplings typically range from about 125 Hz ($CH_3$) to about 200 Hz (aromatic or unsaturated C—H). Thus, to detect these heteronuclear couplings, a few milliseconds or more worth of data need to be collected, i.e., TE×NE should be greater than a few milliseconds. These parameters are well within the acquisition parameters of a typical CPMG measurement, which typically has a TE value in the range of 0.1 ms to a few ms and NE in the range of a few hundreds to a couple thousands. Furthermore, as stated above, TE should be longer than $1/\Delta\omega$. Here, $\Delta\omega$ is the Larmor frequency difference between the $^1H$ and $^{13}C$; the condition TE>$1/\Delta\omega$ can be easily met. For homonuclear couplings between $^1H$ and $^1H$, the scalar couplings range from greater than zero to about 18 Hz. This requires a data collection time (TE×NE) of at least several tens of milliseconds. This requirement is still within the parameters for a standard $^{13}$CPMG measurement. $^1$However, because $\Delta\omega$ is typically small for $^1H$ homonuclear experiments. As a result, TE may not be longer than $1/\Delta\omega$. Therefore, the $^1H$—$^1H$ homonuclear scalar coupling information is often not measurable in a typical CPMG experiment.

In FIG. 6, the 180-degree pulses at the observed nuclei (e.g., $^1H$) frequency permit acquisition of echoes as in a regular CPMG experiment, while the 180-degree pulses at the coupled nuclei (e.g., $^{13}C$) prevent the J-modulated signals from being refocused. The train of 180-degree $^1H$ pulses keep the $^1H$ nuclear spins substantially on the transverse plane. The series of 180-degree pulses refocus spins (reduce loss of coherence due to magnetic field inhomogeneities) and makes it easier to derive the spin-spin (T2) relaxation times from the spin-echo data. The simultaneous 180-degree pulses at the coupled $^{13}C$ frequency invert the $^{13}C$ spin states. This prevents the coupled $^1H$ signals from being refocused. These processes may be better understood using vector diagrams shown in FIGS. 7A and 7B.

Figure 7A:
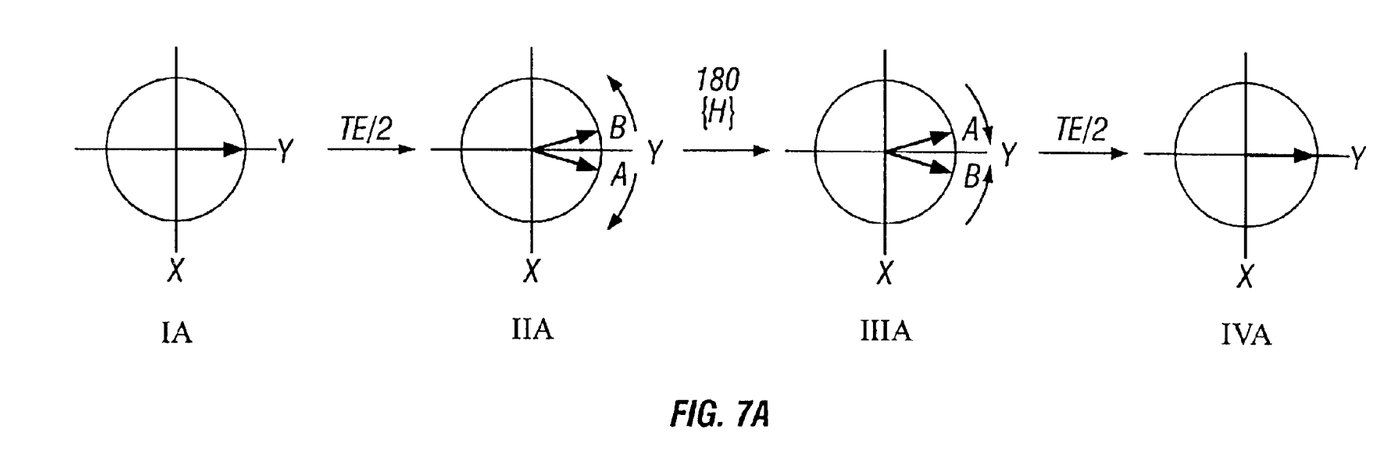
FIGS. 7A and 7B show vector diagrams illustrating spin behaviors according to pulse sequences with and without an inversion pulse in the coupled nuclear channel.

FIG. 7A depicts the spins after a spin-echo sequence without a simultaneous 180-degree inversion pulse at the $^{13}C$ frequency. In FIG. 7A, the observed nuclear signal (e.g., $^1H$) is aligned with the Y axis after a 90-degree pulse in the -X axis direction (state IA). The coupled components in the signal will separate during the first half of the evolution period (TE/2) because each coupled component actually resonates at slightly different frequencies: one at $\omega_0+\pi J$ and the other at $\omega_0-\pi J$, where $\omega_0$ is the average Larmor frequency of the observed signal (or the Larmor frequency in the absence of spin coupling). Assuming the A component has a frequency higher than, and the B component lower than, the average Larmor frequency ($\omega_0$), then, after the first TE/2 delay, the A component is ahead, by ($\pi$ J×TE/2) radians, of a hypothetical average signal resonating at the Larmor frequency ($\pi_0$), which is illustrated as being aligned with the Y axis in a rotating frame. At the same time, the B component lags behind the average signal by ($\pi$J×TE/2) radians (state IIA). If a 180-degree pulse is now applied to the system along the Y axis, the A and B components will be rotated 180 degrees around the Y axis (state IIIA). The net effect is that the A and B components switch position with respect to the hypothetical average signal. In other words, the A component is now ($\pi$J×TE/2) radians behind the average signal, and the B component is now ($\pi$J×$T_E$/2) radians ahead of the average signal (state IIIA). After the second $T_E$/2 delay, the A component (the faster component) will catch up and the B component (the slower component) will fall behind by ($\pi$J×$T_E$/2) radians. As a result, the A and B components will coincide with the hypothetical average signal (state IVA). The net effect is that spin state IVA is identical to spin state IA, as if there were no J modulation. In other words, J modulation will be lost after a simple spin-echo sequence, without a simultaneous inversion pulse at the coupled nuclei ($^{13}C$) frequency.

Figure 7B:
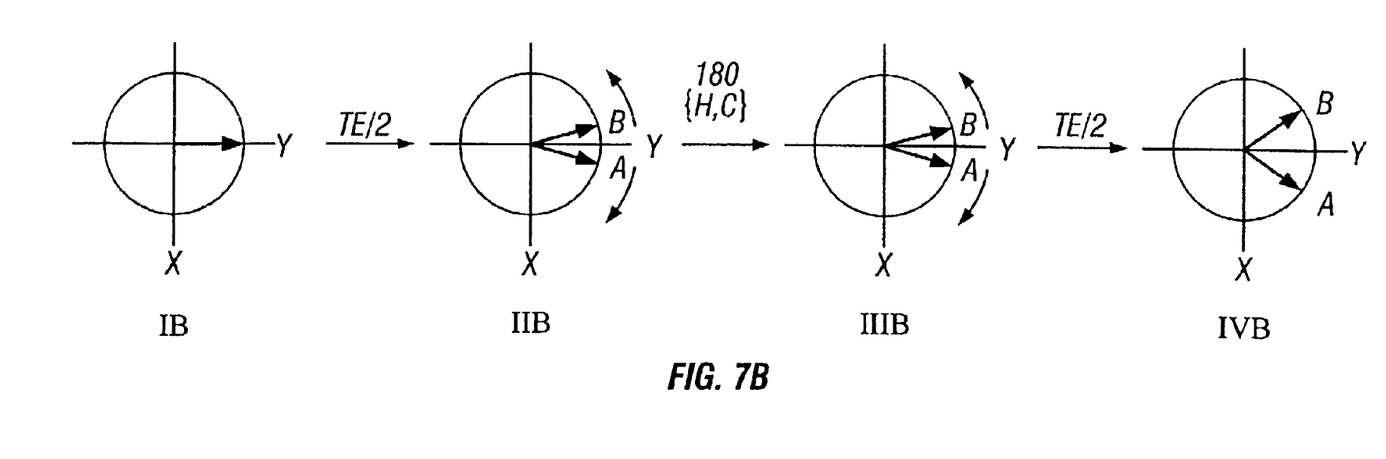

Referring to FIG. 7B, the same spin systems after the first 90-degree pulse and the first TE/2 delay period have the same spin states (states IB and IIB) as those in FIG. 7A (states IA and IIA). If 180-degree inversion pulses are simultaneously applied to both the observed (e.g., $^1H$) and the coupled nuclei (e.g., $^{13}C$, $^{15}N$, or other nucleus), then the resultant spin state is as shown in IIIB. The 180-degree pulse in the $^1H$ channel rotates the A and B components by 180 degrees around the Y axis. However, the 180-degree pulse in the $^{13}C$ channel changes $^{13}C$ spins from a high spin state to a low spin state, and vice versa. As a result, the A component"s $^{13}C$ partner now makes the A component spin slower than the average signal, and the B component"s $^{13}C$ partner makes the B component spin faster than the average signal. As a result of the double switch, spin state IIIB in FIG. 7B is different from spin state IIIA in FIG. 7A. After the second TE/2 delay period, the A and B components, instead of refocusing, separate further. The magnitude of such separation ($\pi$ JTE radians) is a function of the coupling constant (J) and the delay time TE. The spin-echo data acquired after the pulse sequence shown in FIG. 7B includes the J modulation information, i.e., the echo train envelope for the observed $^1H$ signal is modulated by the J-coupling. This J modulation is doubled for the second spin echo, tripled for the third spin echo, and so on, because of the cumulative TE delay.

While the pulses (90-degree pulse and 180-degree pulse) described herein may be simple pulses, in the presence of significant magnetic field inhomogeneity, it might be desirable to use adiabatic or composite pulses for the 90-degree (excitation) and/or 180-degree (refocusing or inversion) pulses or to use a phase-cycled CPMG (PCCPMG) sequence such as XY16, which is a specific pulse sequence where successive refocusing pulses in the same echo train follow a specific phase cycling scheme. One skilled in the art would appreciate that various composite pulses are available to substitute the simple 90-degree and the 180-degree pulses. See M. H. Levitt and R. Freeman, *J. Mag. Reson.* (33), 473 (1979). For example, a composite four-pulse sequence, $$P = \left(\frac{\pi}{4}\right)_{-y}\left(\frac{\pi}{4}\right)_{x}\left(\frac{\pi}{4}\right)_{y}\left(\frac{\pi}{4}\right)_{x}$$

is commonly used as a substitute for a 90-degree pulse in the X-axis direction, $(\pi/2)_x$. See M. H. Levitt, *J. Mag. Reson.* (48), 234 (1982). Similarly, a 180-degree pulse, may be substituted by, for example, the following composite pulse:

$$P = \left(\frac{\pi}{2}\right)_{x}(\pi)_{y}\left(\frac{\pi}{2}\right)_{x}$$

In this notation, the ($\pi/2$) indicates the degrees (e.g., 90 degrees=$\pi/2$) of the pulses and the subscript indicates the phase of the pulses. See M. H. Levitt, *J. Mag. Reson.* (48), 234 (1982). A phase-cycled $^{13}$CPMG sequence is better than those using simple or composite 90-degree or 180-degree pulses, when there is inhomogeneity in $B_o$ and $B_1$ and one wants to keep the magnetization mainly in the longitudinal direction while continuously inverting them, as for the coupled nuclei (e.g., $^{13}$C) in the heteronuclear J modulation experiments described herein.

The acquired data (echo train) may be separated into a modulated and an unmodulated parts, e.g., by any inversion method known in the art. Such separation is possible because the unmodulated part comprises simple exponential decay functions, while the modulated part comprises sinusoidal (or cosinusoidal) functions. Alternatively, the unmodulated part may be removed by subtracting data acquired without the 180-degree inversion pulses at the $^{13}$C frequency (data without J modulation) from data acquired with the 180-degree inversion pulses in the $^{13}$C channel (data with J-modulation). This technique is known as a difference measurement (or difference spectroscopy). The difference spectroscopy approach may be preferable when the modulated part is relatively insignificant as compared to the unmodulated part in the acquired data. In yet another approach, Fourier transformation (FT) or fast Fourier transformation (FFT) may be used to separate the modulated part from the unmodulated part in the NMR data.

Figure 8:
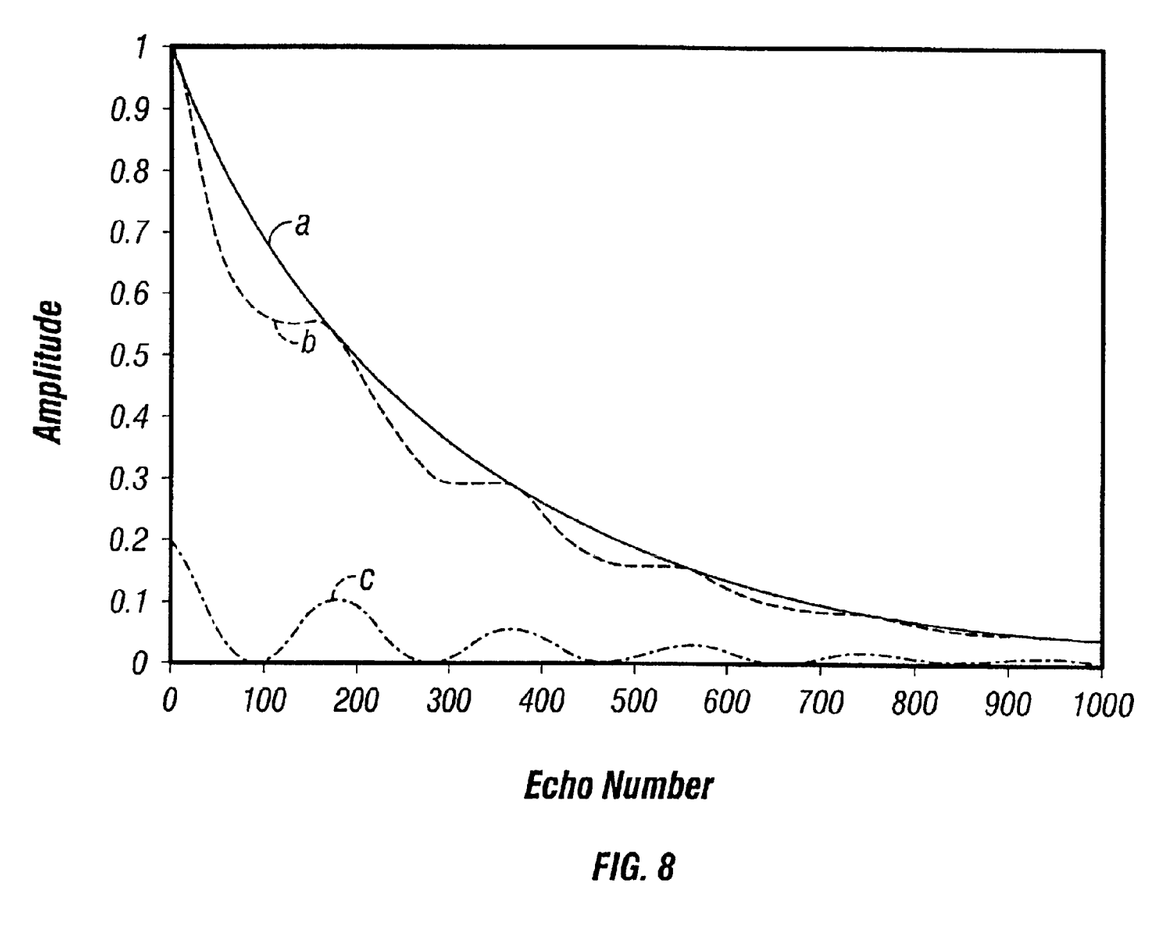
FIG. 8 shows a graph illustrating a difference spectroscopy.

FIG. 8 illustrates a difference spectroscopy. As shown in FIG. 8, curve a represents amplitudes of echoes in an echo train in the absence of J modulation and curve b represents amplitudes in an echo train with J modulation. The J modulation in curve b is apparent from the sinusoidal modulation of the otherwise exponential curve. Subtracting curve a from curve b yields curve c, which includes only J modulation. In the absence of the unmodulated part (a), curve c can be readily analyzed for the coupling information (i.e, from the periodicity of the sinusoidal waves). While this example shows only one sinusoidal modulation, well logging data may include many different sinusoidal modulations. Multiple sinusoidal functions may be deconvoluted by Fourier transformation to yield various periodicities, from which various J coupling constants may be extracted and used to characterize formation fluids. In this example, it is assumed that 10% of the detected signals are modulated by J couplings. However, with actual $^1$H—$^{13}$C couplings at the natural abundance, there will only be 1.1% coupled species. Nevertheless, the echo trains and the difference spectra may be analyzed as illustrated.

In addition to using the J-coupling information to derive formation properties, the J-coupling information may also be correlated (e.g., using multidimensional measurements) with other parameters such as T1, T2, T1 /T2 (a ratio of T1 over T2), diffusion, and, if sufficient field homogeneity can be achieved, chemical shift information. One skilled in the art would appreciate how these other parameters may be obtained and correlated with the information obtained from J-modulation. For example, if J-modulation information is correlated with diffusion, e.g., using diffusion editing techniques, separate diffusion spectra may be obtained for every resonance. For diffusion editing techniques, see U.S. patent application Ser. No. 09/723,803 filed on Nov. 28, 2000 by Hürlimann et al., entitled "Simpler and More Robust Hydrocarbon Typing with Pulsed NMR," and Hürlimann, et al., "*Diffusion Editing. New NMR Measurement of Saturation and Pore Geometry*," Society of Professional Well Log Analysts Annual Meeting, Jun. 5, 2002. Diffusion measurements could use switched gradients. Because molecular diffusion is a function of molecular size (molecular weight), correlating diffusion information with J modulation information makes it possible, for example, to separate molecular weights of aromatic molecules from molecular weights of aliphatic molecules (based on their differing J couplings), which in turn could be used to estimate the asphaltene content.

Similarly, J modulation information may be correlated with information from chemical exchanges (e.g., from bound state to free fluid state). Depending on the rates of chemical exchanges, the signals of the same molecule in two different environments may appear as separate signals or as unresolved resonances. Many experiments are available to investigate the exchange processes. For example, exchange between unresolved resonances may be monitored using multidimensional measurements, or variants thereof. For example, correlation with exchange may be obtained with the following pulse sequence: CPMG($^1$H, $^{13}$C) $T_{90}\tau_{mix}$CPMG($^1$H, $^{13}$C), where CPMG($^1$H, $^{13}$C) is the basic sequence shown above in FIG. 6 and $T_{90}$ is a 90-degree pulse. In this sequence, the first CPMG($^1$H, $^{13}$C) acquires a J-modulated data set as described above. The $T_{90}$ pulse converts the transverse magnetization into polarization that is stored during $\tau_{mix}$ and is read out by the second CPMG ($^1$H, $^{13}$C) pulse sequence. The second spin-echo data set includes transfer/exchange of polarization that occurred during $\tau_{mix}$. Two-dimensional fast Fourier transformation (FFT) over the two echo trains would yield information on the exchange.

Furthermore, the J coupling information may be used in combination with other measured properties of formation fluids, such as compositional information (e.g., gas contents, oil contents, etc.), mechanical properties (e.g., density and viscosity), optical properties (e.g., reflectivity), and electrical properties (e.g., resistivity, electromagnetic inductivity), in addition to the NMR properties (e.g., $T_1$ and $T_2$ relaxations, diffusion, exchange rates). One skilled in the art would appreciate how these properties may be measured and used to predict formation fluid properties.

Useful nuclei pairs for J-spectroscopy include $^1$H—$^{13}$C for oil characterization with J-couplings between 100 and 200 Hz (e.g., CH$_3$, about 125 Hz, aromatic CH about 150 Hz), $^1$H—$^{17}$O for water characterization, and $^1$H—$^{15}$N for amines characterization. $^1$However, these useful nuclei are present in low abundance—$^{13}$C about 1.1%, $^{17}$O about 0.038%, and N about 0.37%. If J-modulation is observed on the $^1$H signal, the fraction of the signal that is modulated would be very small. As stated above, difference measurements, in which the unmodulated part is cancelled, may be used to facilitate data analysis.

Alternatively, J modulation may be observed on the $^{13}$C signals (instead on the $^1$H signals). This is often referred to as "reverse" detection. The advantage of this alternative approach is that most signals are modulated by $^1$H and there is little unmodulated part in the acquired data. On the other hand, the lower gyromagnetic ratio of $^{13}$C (about ¼ of that of $^1$H) means $^{13}$C observation is less sensitive than $^1$H observation. Thus, it is more difficult to achieve the signal to noise ratio (S/N) necessary for inversion analysis. The lower S/N of $^{13}$C observation may be enhanced by polarization transfer or cross polarization from the surrounding protons.

Cross polarization (or polarization transfer) is a process by which the presence of dipolar coupling between rare spins (e.g., $^{13}$C) and abundant nuclei (e.g., $^1$H) in solid, or the presence of scalar (J) coupling in liquids can be exploited to provide signal enhancement under appropriate conditions. The maximum achievable enhancements typically correspond to the ratio of the gyromagnetic ratio of the abundant nuclei over that of the rare nuclei (e.g., $\gamma_H/\gamma_C \approx 4$). With liquid samples, polarization transfer may be achieved by simple approaches such as NOE (nuclear Overhauser effect) or more sophisticated experiments such as INEP (insensitive nuclei enhanced by polarization transfer) or DEPT (distortionless enhancement by polarization transfer). See S. W. Homans, *A Dictionary of Concepts in NMR*, Revised Ed., pp. 91-93, 170-172, and 207-211, Oxford Science Publication, $^{13}$Clarendon Press, Oxford, UK, 1992; see also U.S. Pat. No. 5,677,628 issued to Watanabe et al. While INEPT and DEPT involve series of pulses and delays as outlined in the Watanabe patent and Homans reference, NOE experiments can be accomplished by a single saturation pulse (or its variants, e.g., composite pulses). These pulses will be generally referred to herein as "polarization transfer" pulses.

In an NMR spectrum obtained in a homogeneous magnetic field, the signal line width correlates with 1/T2. If the line width is on the order of the coupling constant or larger, then the peaks cannot be resolved. Because fluid viscosity affects T2, there is a maximum viscosity above which the J-spectrum cannot be resolved. For proton observations, this limit may be on the order of about 200 centipoises (cp). Because the $J_{CH}$ couplings are significantly larger, it is possible to observe $^{13}$C resonance and obtain J coupling information in relatively viscous liquids. Thus, it might be advantageous to use direct detection (observe $^1$H signals) with low viscosity fluids and reverse detection (observe $^{13}$C signals) with high viscosity fluids.

Figure 9:
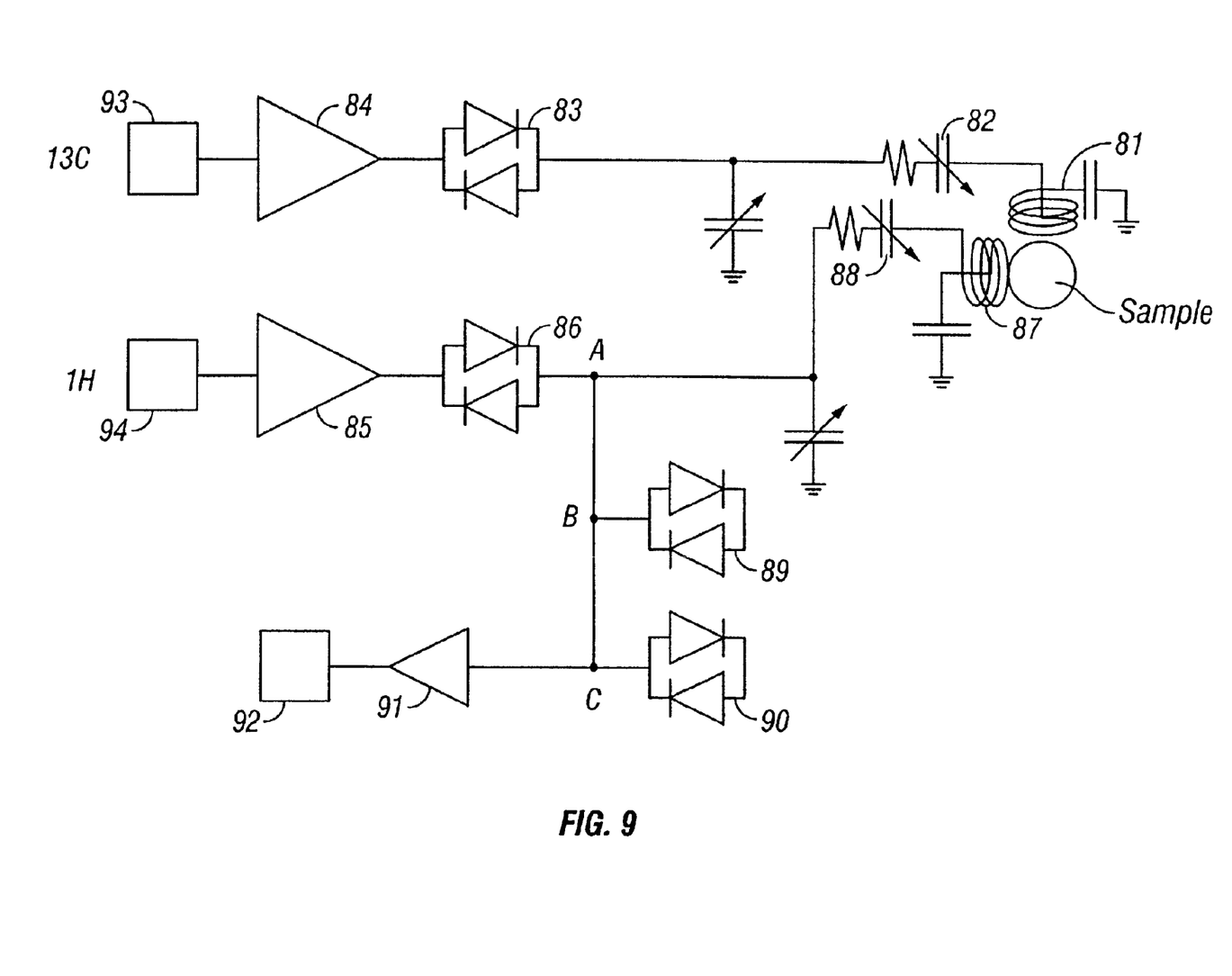
FIG. 9 shows a probe configuration according to one embodiment of the invention.

Embodiments of the invention may use NMR tools having configurations similar to those of NMR tools used in the art. FIG. 9 shows one embodiment of device/probe configurations according to the invention. This probe may be part of a well logging tool or a formation fluid sampling tool. The NMR probe further comprises electronic components (not shown) for controlling pulse sequences and data acquisition. The electronic components may further communicate with computers in the logging tool or the formation fluid sampling tool or on the surface of the earth. The probe as illustrated has two channels, $^1$H and $^{13}$C. The probe shown in FIG. 9 is for $^1$H observation and $^{13}$C coupling. In a conventional spectrometer, the $^1$H channel is referred to as the observation channel and the $^{13}$C channel the "decoupling" channel, the purpose of which is to remove coupling effects. This is opposite to the purpose of the $^{13}$C channel of the present invention, which is used to develop J couplings. According to embodiments of the invention, the $^{13}$C channel is for the inversion of the "coupled" $^{13}$C nuclei. Therefore, the $^{13}$C channel as shown will be referred to herein as the "coupled" channel. One skilled in the art would appreciate that other combination of channels are possible, e.g., $^1$H and $^{17}$O, or $^1$H and $^{31}$P, without departing from the scope of the invention. Furthermore, a probe according to embodiments of the invention may also be used for "reversed" detection, in which the $^{13}$C channel is the observation channel and the $^1$H channel is the coupled channel.

As shown in FIG. 9, the coupled ($^{13}$C) channel has an antenna 81 tuned to a $^{13}$C resonance frequency at the selected magnetic field strength. One skilled in the art would appreciate that a proper $^{13}$C frequency for this purpose may be a frequency close to the average frequency of all expected 13C signals, typically this frequency corresponds to the center of the "observation" or "decoupling" frequency window. The antenna 81 may comprise a wire coil (solenoid antenna), and, in the case of a logging tool, may further include a core comprising a magnetically susceptible material, such as ferrite. Alternatively, the antenna may comprise any other types of antennae known in the art, such as a double-saddle antenna. The antenna is connected to a tunable capacitor 82, which permits fine tuning of the responsive frequency of the antenna 81. The circuit also includes a crossed diode 83. The crossed diode 83 functions to isolate the preamp while pulsing and to isolate the power amplifier while detecting. The circuit is connected to a $^{13}$C power amplifier 84, which is in turn connected to a transmitter 93 capable of transmitting a radio frequency (RF) corresponding to the $^{13}$C resonance frequency. A transmitter for this purpose typically comprises a frequency synthesizer/generator and a pulse programmer/controller, which is used to control the pulse shapes/patterns. One skilled in the art would appreciate that any device capable of generating RF waves with specific frequencies in a controlled fashion may be used as a transmitter in the embodiments of the invention.

The $^1$H channel has a similar circuit ("transmitter circuit") for transmitting an RF frequency from a transmitter 94 that is coupled to a $^1$H power amplifier 85 and a crossed diode 86 to the $^1$H tuned coil (antenna) 87. Again, the antenna may comprise wire coils, that may or may not include a core of magnetically susceptible material (e.g., ferrite). The antenna 87 may be tuned to a $^1$H resonance frequency that is close to the average frequency of the observed $^1$H signals. A tunable capacitor 88 is in line for tuning purpose. As stated above, transmitter 94 may comprise a frequency synthesizer/generator and a pulse programmer/controller. Further, transmitter 94 for the $^1$H channel may or may not be the same physically units as transmitter 93 for the $^{13}$C channel. For example, the same pulse programmer may be used to control both channels, and the same frequency synthesizer may be used to produce a frequency which is then further manipulated (by summation and/or subtraction with other frequencies) to produce both the $^1$H and the $^{13}$C frequencies. Similarly, the same pulse programmer/controller may be used to control both $^1$H and $^{13}$C pulses. One skilled in the art would appreciate how this may be achieved.

As illustrated in this example, the orientation of the $^1$H antenna 87 is orthogonal to that of the $^{13}$C antenna 81. Both antenna 87 and antenna 81 are placed adjacent to the sample. The orthogonal configuration, which is desirable but not necessary, helps to minimize interference between the two antennae (coils). In addition to the configuration of orthogonal solenoid coils as shown in FIG. 9, other configurations or types of antenna that can produce low interference between the observed and the coupled antennae may also be used. For example, a saddle antenna, a loop antenna, and/or a solenoid coil antenna may be combined in an arrangement that minimizes the interference. A saddle coil (saddle antenna) is a loop coil (loop antenna) wrapped around an object, which is typically in a cylindrical form, to form a saddle shape. Thus, a saddle coil has two co-axial arcs and two parallel lines. A saddle antenna often includes a pair of saddle coils, i.e., a double-saddle antenna.

FIG. 9 illustrates separate antennas for the $^1$H and the $^{13}$C channels. $^1$However, one skilled in the art would appreciate that these two antennas may be replaced with a single antenna that is coupled to a double resonance circuit. Double tuned coils (antennas) are well known in the art. See V. R. Cross, R. K. Hester, and J. S. Waugh, Rev. Sci. Instrum., vol. 47, *"Single Coil Probe with Transmission-Line Tuning for Nuclear Magnetic Double Resonance"*, p. 1486 (1976); F. D. Doty, R. R. Inners, and P. D. Ellis, J. Mag. Res., vol. 43, *"A Multinuclear Double Tuned Probe for Applications with Solids or Liquids Utilizing Lumped Tuning Elements"*, p. 399 (1981); and U.S. Pat. No. 5,162,739 issued to Doty. The antenna(s), whether a single antenna coupled to a double resonance circuit or two independent antennas, to be used in embodiments of the invention will be generally referred to as an "antenna assembly."

Referring to FIG. 9, the $^1$H channel (the observation channel) also includes an additional circuit ("receiver circuit") that permits the $^1$H antenna to function as a receiver. One skilled in the art would appreciate the same antenna may be used to induce an RF magnetic field and then to detect the resultant NMR signals. The receiver circuit and the transmitter circuit joint at point A. A first crossed diode 89 is connect in parallel in this circuit at point B, which is separated from point A by a distance that is equal to a quarter wavelength ($\lambda/4$) of the RF wave for the $^1$H resonance frequency. The quarter wavelength ($\lambda/4$) cable is to isolate the receiver circuit from the transmitter when it is pulsing and also to isolate the transmitter from the receiver when acquiring. In addition, a second crossed diode 90 is connected in parallel in the receiver circuit at point C, which is separated from point B by a distance that is equal to a quarter wavelength ($\lambda/4$) of the RF wave for the $^{13}$C resonance frequency. These crossed diodes 89 & 90 prevent strong RF pulses from reaching the preamplifier 91 connected to the $^1$H receiver 92 and permit the detection of weak $^1$H signals. FIG. 9 describes a setup for $^1$H observation. One skilled in the art would appreciate that the $^1$H and $^{13}$C channels may be reversed in the reverse detection mode.

Embodiments of the present invention may be used in a well logging tool or a formation fluid sampling tool. As a well logging tool, embodiments of the invention may be used in a wireline tool that is adapted to be lowered into a wellbore on an electric cable or a logging-while-drilling (LWD or MWD) tool that is part of a drilling tool assembly. Embodiments of the invention are applicable to homonuclear scalar couplings as well as heteronuclear scalar couplings. While the above example uses $^{13}$C (carbon-13) as the hetero coupled nucleus for illustration, one skilled in the art would appreciate that couplings involving other heteronuclear species, such as nitrogen-15 ($^{15}$N), oxygen-17 ($^{17}$O), and phosphorus-31 ($^{31}$P), may also be used according to embodiments of the invention. In addition, the observed nucleus may be one of these hetero (non-proton) nuclear species instead of $^1$H in the reverse detection mode.

While the invention has been described with respect to a limited number of embodiments, those skilled in the art, having benefit of this disclosure, will appreciate that other embodiments can be devised without departing from the scope of the invention as disclosed herein. Accordingly, the scope of the invention should be limited only by the attached claims.

What is claimed is:

1. A nuclear magnetic resonance instrument, comprising:
   a housing adapted to move in a wellbore drilled through earth formations; a magnet disposed in the housing adapted to induce a static magnetic field having a selected magnetic field strength in a zone of interest;
   an antenna assembly disposed in the housing, the antenna assembly adapted to resonate at a first frequency and a second frequency, the first frequency corresponding to a resonance frequency of a first nucleus at the selected magnetic field strength, the second frequency corresponding to a resonance frequency of a second nucleus at the selected magnetic field strength, wherein the first nucleus is different from the second nucleus;
   means for inducing a radio frequency magnetic field, according to a first and a second substantially simultaneous pulse sequences associated with the first and second nucleus, in the zone of interest, the means for inducing the radio frequency magnetic field being operatively coupled to the antenna assembly; and
   means for detecting nuclear magnetic resonance signals at the first frequency, the means for detecting being operatively coupled to the antenna assembly.

2. The instrument of claim 1, wherein the first nucleus is a proton.

3. The instrument of claim 1, wherein the second nucleus is carbon-13.

4. The instrument of claim 1, wherein the second nucleus is oxygen-17.

5. The instrument of claim 1, wherein the second nucleus is phosphorus-31.

6. The instrument of claim 1, wherein the zone of interest is in the earth formations surrounding the wellbore.

7. The instrument of claim 6, wherein the housing is adapted to be lowered into the wellbore on an electric cable.

8. The instrument of claim 6, wherein the housing forms part of a drilling tool assembly.

9. The instrument of claim 1, wherein the housing forms part of a formation fluid sampling tool and the zone of interest is inside the formation fluid sampling tool.

10. The instrument of claim 1, wherein the antenna assembly comprises an antenna coupled to a double resonance circuit.

11. The instrument of claim 1, wherein the antenna assembly comprises a first antenna and a second antenna.

12. The instrument of claim 10, wherein the first antenna and the second antenna are substantially orthogonal to each other.

13. The instrument of claim 10, wherein at least one of the first antenna and the second antenna comprises one selected from a saddle antenna and a loop antenna.

14. The instrument of claim 10, wherein the first antenna is selectively connected to a circuit adapted to transmit a radio frequency wave having the first frequency and the second antenna is selectively connected to a circuit adapted to transmit a radio frequency wave having the second frequency.

15. The instrument of claim 1 wherein the selected pulse sequence comprises a Carr-Purcell-Meiboom-Gill pulse sequence at the first frequency and an 180-degree pulse train at the second frequency.

16. A nuclear magnetic resonance instrument, comprising:
   a housing adapted to move in a wellbore drilled through earth formations;
   a magnet disposed in tire housing adapted to induce a static magnetic field having a selected magnetic field strength in a zone of interest;
   means for inducing a first radio frequency magnetic field in the zone of interest at a first frequency, the first frequency being a resonance frequency of a first nucleus at the selected magnetic field strength;

means for inducing, substantially simultaneous with the first radio frequency magnetic field, a second radio frequency magnetic field in the zone of interest at a second frequency, the second frequency being a resonance frequency of a second nucleus at the selected magnetic field strength, wherein the first nucleus is different from the second nucleus, field; and means for detecting nuclear magnetic resonance signals at the first frequency.

17. The instrument of claim 16, wherein the zone of interest is in the earth formations surrounding the wellbore.

18. The instrument of claim 16, wherein the housing forms part of a formation fluid sampling tool and the Zone of interest is inside the formation fluid sampling tool.

19. A nuclear magnetic resonance instrument, comprising:
a housing adapted to move in a wellbore drilled through earth formations;
a magnet disposed in the housing adapted to induce a static magnetic field having a selected magnetic field strength in a zone of interest;
an antenna disposed in the housing, the antenna being adapted to resonate at a frequency corresponding to a resonance frequency of a first nucleus at the selected magnetic field strength, wherein the nucleus is not a proton;
means for producing a polarization transfer pulse sequence and a Carr-Purcell-Meiboom-Gill pulse sequence, the means for producing being operatively coupled to the antenna, wherein the polarization transfer pulse Sequence comprises a first pulse sequence associated with the first nucleus and a substantially simultaneous second pulse sequence associated with a second nucleus; and
means for detecting nuclear magnetic resonance signals.

20. The instrument of claim 19, wherein the zone of interest is in the earth formations surrounding the wellbore.

21. The instrument of claim 19, wherein the housing is part of a formation fluid sampling tool and the zone of interest is inside the formation fluid sampling tool.

22. A method for determining a formation fluid property using a nuclear magnetic resonance instrument in a wellbore, comprising:
inducing a static magnetic field having a selected magnetic field strength in a formation fluid sample;
acquiring nuclear magnetic resonance measurements having J coupling information using the nuclear magnetic resonance instrument; and
deriving the J coupling information from the nuclear magnetic resonance measurements.

23. The method of claim 22, wherein the formation fluid sample comprises connate fluids withdrawn into a sample tube of the nuclear magnetic resonance instrument in a formation fluid sampling tool.

24. The method of claim 22, wherein the formation fluid sample comprises connate fluids in earth formations surrounding the wellbore.

25. The method of claim 22 wherein the acquiring comprises collecting nuclear magnetic resonance data using a pulse sequence that includes a Carr-Purcell-Meiboom-Gill pulse sequence.

26. The method of claim 22 wherein the acquiring comprises collecting nuclear magnetic resonance data using a pulse sequence that includes a phase-cycled Carr-Purcell-Meiboom-Gill pulse sequence.

27. The method of claim 22, wherein the J coupling comprises homonuclear J coupling.

28. The method of claim 22, wherein the S coupling comprises heteronuclear J coupling.

29. The method of claim 28, wherein the acquiring comprises
(a) applying an excitation pulse at a first frequency, the first frequency being a resonance frequency of a first nucleus at the selected magnetic field strength;
(b) waiting for a selected delay time;
(c) simultaneously applying a refocusing pulse at the first frequency and a inversion pulse at a second frequency, the second frequency being a resonance frequency of a second nucleus at the selected magnetic field strength, the first nucleus being different from the second nucleus;
(d) waiting for the selected delay time; and
(e) recording signals at the first frequency.

30. The method of claim 29, wherein the recording lasts for a duration shorter than the selected delay time.

31. The method of claim 30, further comprising: repeating, for a predetermined number of times, (c) through (e) alter a duration that substantially equals the selected delay time has elapsed since start of the recording.

32. The method of 29, wherein at least one of the excitation pulse, the refocusing pulse at the first frequency, and the inversion pulse at the second frequency comprises a composite pulse.

33. The method of claim 29, wherein the acquiring comprises collecting nuclear magnetic resonance data using a reverse-detection pulse sequence.

34. The method of claim 33, wherein the reverse-detection pulse sequence further comprises a polarization transfer pulse sequence.

35. The method of claim 29, wherein the acquiring comprises using a pulse sequence comprising one selected from an inversion-recovery pulse sequence and a saturation-recovery pulse sequence.

36. The method of claim 29, wherein the deriving comprises separating a J coupling modulated part from an unmodulated part in the nuclear magnetic resonance measurements.

37. The method of claim 36, wherein the separating is performed with Fourier transformation.

38. The method of claim 29, wherein the deriving comprises obtaining a difference measurement.

39. The method of claim 29, further comprising estimating a formation fluid property from the J coupling information.

40. The method of claim 39, wherein the estimating further comprises using, in combination with the J coupling information, at least one parameter selected from a spin-lattice relaxation time, a spin-spin relaxation time, a ratio of spin-lattice relaxation time and spin-spin relaxation time, and a diffusion constant.

41. The method of claim 39, wherein the estimating further comprises using, in combination with the J coupling information, at least one parameter selected from compositional information, Optical properties, mechanical properties, electrical properties, and nuclear magnetic resonance properties.

42. A method for estimating a volume fraction of oils in earth formation fluids, comprising:
acquiring nuclear magnetic resonance measurements having carbon-hydrogen J coupling information;
separating a J coupling modulated part from an unmodulated part in the nuclear magnetic resonance measurements; and
determining the volume fraction of oils in the earth formation fluids by comparing a total magnitude of the J coupling modulated part to a total magnitude of the nuclear magnetic resonance measurements.

* * * * *